United States Patent [19]
Billiar et al.

[11] Patent Number: 5,882,908
[45] Date of Patent: Mar. 16, 1999

[54] ISOLATED HUMAN INDUCIBLE NITRIC OXIDE SYNTHASE

[75] Inventors: Timothy R.. Billiar; Andreas K. Nussler; David A. Geller; Richard L. Simmons, all of Pittsburgh, Pa.

[73] Assignee: University of Pittsburgh of the Commonwealth System of Higher Education, Pittsburgh, Pa.

[21] Appl. No.: 465,522

[22] Filed: Jun. 5, 1995

Related U.S. Application Data

[62] Division of Ser. No. 314,917, Sep. 28, 1994, Pat. No. 5,468,630, which is a continuation of Ser. No. 981,344, Nov. 25, 1992, abandoned.

[51] Int. Cl.$^6$ ............ C12N 9/02; C12N 15/53; C12N 15/70
[52] U.S. Cl. ............ 435/189; 435/69.1; 435/69.7; 435/252.3; 435/320.1; 536/23.2; 935/14; 935/29; 935/72
[58] Field of Search ............ 435/191, 192, 435/189, 69.1, 252.3, 69.7; 536/23.2, 23.4

[56] References Cited

U.S. PATENT DOCUMENTS

| | | | |
|---|---|---|---|
| 4,652,639 | 3/1987 | Stabinsky | 536/27 |
| 5,132,407 | 7/1992 | Stuehr et al. | 530/395 |
| 5,268,465 | 12/1993 | Bvedt et al. | 435/252.3 |
| 5,468,630 | 11/1995 | Billiur et al. | 536/25.2 |

OTHER PUBLICATIONS

Nussler, et al., 1992; Inducible Human Hepatocyte Nitric Oxide Synthase: Cloning of the Gene and its Regulation by Cytokines and LPS; J. Leukocyte Biology; Supplement 3, 1992, 29th National Meeting, Society for Leukocyte Biology, Dec. 2–5 1992.

Nussler, et al., 1992, FASEB Meeting; Anaheim, CA; Stimulation of Nitric Oxide in Hepatocytes by Cytokines; Abst. 5200.

Lowenstein, et al; Aug. 1992; Cloned and expressed macrophage nitric oxide synthase contrasts with the brain enzyme; Proc. Natl. Acad. Sci, USA; vol. 89, pp. 6711–6715.

Bredt, et al; 1991; Cloned and expressed nitric oxide synthase structurally resembles cytochrome P–450 reductase; Nature; vol. 351. pp. 714–718.

Kie, et al; 1992; Cloning and Characterization of Inducible Nitric Oxide Synthase from Mouse Macrophages; Science; vol. 256, pp. 225–228.

Marsden, et al; 1992; Molecular cloning and characterization of human endothelial nitric oxide; Elsevier Science publishers B.V.; vol. 307, pp. 287–293.

Palmer, et al; 1987; Nitric oxide release accounts for the biological activity of endothelium–derived relaxing factor; Nature 327: 524–526.

Ignarro, et al; 1987; Endothelium–derived relaxing factor produced and released from artery and vein in nitric oxide; Proc. Natl. Acad. Sci. USA. 84: 9265–9269.

Bredt and Snyder; 1989; Nitric Oxide mediates glutamate–linked enhancement of cGMP levels in the cerebellum; Proc. Natl. Acad. Sci. USA, 86: 9030–9033.

Burnett, et al; 1992; Nitric Oxide: A Physiologic Mediator of Penile Erection; Science; 257: 401–403.

Granger, et al; 1987; Specific Amino Acid (L–Arginine) Requirement for the Microbiostatic Activity of Murine Macrophages; J. Clin. Invest. 81: 1129–1136.

Hibbs, Jr., et al; 1987; Macrophage Cytotoxicity: Role for L–Arginine Deiminase and Imino Nitrogen Oxidation to Nitrite; 235: 473–476.

Busse and Mulsch; 1990; Calcium–dependent nitric oxide synthesis in endothelial cytosol is mediated by calmodulin; FEBS Letters 265: 133–136.

Kilbourn, et al; 1990; $N^6$–Methyl–Larginine inhibits tumor necrosis factor–induced hypotension: Implications for the involvement of nitric oxide; Proc. Natl. Acad. Sci. USA; vol. 87: 3629–3632.

Mulligan, et al; 1992; Lung Injury After Deposition of IgA Immune Complexes; J. Immunology; 148: 3086–3092.

Corbett, et al; 1991; Interleukin–1β–induced Formation of EPR–detectable Iron–Nitrosyl Complexes in Islets of Langerhans; J. Biol. Chem. 266: 21351–21354.

Summers and Smith, 1988, A Manual of Methods For Baculovirus Vectors and Insert Cell Culture Procedures; Texas Agricultviral Experiment Station Bulletin No. 1555.

Curran, et al; 1991; Nitric oxide and nitric oxide–generating compounds inhibit hepatocyte protein synthesis; FEBS Letters 5: 2085–2092.

Billiar, et al., 1992, Association Between Synthesis and Release of CGMP and Nitric Oxide Biosynthesis by Hepatocytes, Amer. Physiol. Soc., C1077–C1082.

Drapier, J.C., 1991, Res.Immoc. 39th Forum In Immunol; See specifically pp. 557, 562 and 589–590.

Bredt and Snyder, 1990, Isolation of Nitric Oxide Synthetase, a Calmodulin–Requiring Enzyme Proc. Natl. Acad. Sci., 87: 682–685.

Billiar, et al., 1991, Cytokine–Induced Synthesis and Release of cGMP by Hepatocytes is Mediated by Nitric Oxide, FASEB Journ. 5 (5): A1344, Ab. No. 5642.

Knowles, et al., 1990, Anti–Inflammatory Glucocorticoids Inhibit the Induction by Endotoxin of Nitric Oxide Synthase in the Lung, Liver, and Aorta of the Rat, Biochem. and Biophys. Resch. Commun., 172 (3): 1042–1048.

Stadler, et al., 1991, Effect of Endogenous Nitric Oxide on Mitochondrial Respiration of Rat Hepatocytes In Vitro and In Vivo, Arch. Surg., vol. 126 (2): 186–191.

Nathan, 1991, A Commentary: Inducible Nitric Oxide Synthase, Research Immunol. 142 (7): 600–602.

(List continued on next page.)

*Primary Examiner*—Robert A. Wax
*Assistant Examiner*—William W. Moore
*Attorney, Agent, or Firm*—Leydig, Voit & Mayer, Ltd.

[57] ABSTRACT

A human tissue inducible nitric oxide synthase cDNA clone is disclosed. A process for preparing this cDNA clone coding for human tissue inducible nitric oxide synthase and for expressing the human tissue inducible nitric oxide synthase protein are provided.

11 Claims, No Drawings

OTHER PUBLICATIONS

Wright, et al., 1992, Protective and Pathological Roles of Nitric Oxide in Endotoxin Shock, Cardiovascular Resch., 26 (1): 48–57.

Di Silvio, et al., 1992, Impairment of Nitric Oxide Synthesis by Hepatocytes from Chronic Ethanol Treated Animals, Gastroenterology 102: A801.

Klatt, et al., 1992, $Ca^{2+}$/Calmodulin–Dependent Cytochrome C Reductase Activity of Brain Nitric Oxide Synthase, J. Biol. Chem. 267(16): 11374–11378.

Harbrecht, et al., 1992, Inhibition of Nitric Oxide Synthesis During Endotoxemia Promotes Intrahepatic Thrombosis and an Oxygen Radical–Mediated Hepatic Injury, Journ. of Leukocyte Biology, 52 (4): 390–394.

Harbrecht, et al., 1992, Nitric Oxide Synthesis Serves to Reduce Hepatic Damage During Acute Murine Endotoxemia, Critical Care Medicine, 20 (11): 1568–1574.

Fortkamp, et al., 1986, Cloning and Expression in *Escherichia Coli* of a Synthetic DNA for Hirudin, the Blood Coagulation Inhibitor in the Leech, DNA 5: 511–517.

Oguchi, et al., 1992, Induction of $Ca^{2+}$/Calmodulin–Dependent NO Synthase in Various Organs of Rats by Propionibacterium Acnes and Lipopolysaccharide Treatment, FEBS Letters 308 (1): 22–25.

Hevel, et al., 1991, Purification of the Inducible Murine Macrophage Nitric Oxide Synthase, J. Biol. Chem. 266(34): 22789–22791.

Hibbs, et al., 1992, Evidence for Cytokine–Inducible Nitric Oxide Synthesis from L–Arginine in Patients Receiving Interleukin–2 Therapy, J. Clin. Invest. 89: 867–877.

Billiar, et al., 1991, Two Unique Aspects of Inducible .N=0 Synthase in Liver Cells and Accessory Cells: Hepatic Damage is Minimized by Hepatocyte .N=0 Production and Immunoregulation is Mediated by Macrophase .N=0 Production, Resch. in Immunol. 142: 584–586.

Oshima, et al., 1992, Purificationi of Nitric Oxide Syntheses from Bovine Brain: Immunological Characterization and Tissue Distribution, Biochem. and Biophys. Resch. Commun., vol. 183 (1): 238–244.

Denis, 1991, Tumor Necrosis Factor and Granulocyte Macrophage–Colony Stimulating Factor Stimulate Human Macrophages to Restrict Growth of Virulent Mycobacterium Avium and to Kill Avirulent M. Avium: Killing Effector Mechanism Depends on the Generation of Reactive Nitrogen Intermediates, Journ. of Leukocyte Biol., vol. 49: 380–387.

Hunt and Goldin, 1992, Nitric Oxide Production by Monocytes in Alcholic Liver Dusease, Journ. of Hepatology, vol. 14: 146–150.

Munoz–Fernandez, et al., 1992, Activation of Human Macrophages for the Killing of Intracellular Trypanosoma Cruzi by TNF–γ and IFN–γ Through a Nitric Oxide–Dependent Mechanism, Immunol. Ltrs., 33: 35–40.

Cameron, et al., 1990, Human Alveolar and Peritoneal Macrophages Mediate Fungistasis Independently of L–Arginine Oxidation to Nitrite or Nitrate, Amer. Review of Respiratory Disease, 142: 1313–1319.

Sherman, et al., 1991, Cytokine–and Pneumocystis Carinii–Induced L–Arginine Oxidation by Murine and Human Pulmonary Alveolar Macrophages, J. Protozool., 38 (6): 234S–236S.

James, et al., 1990, Activation of Human Monocyte–Derived Macrophages to Kill Schistosomula of Schistosoma Mansoni In Vitro, J. Immunol. 145 (8): 2686–2690.

Padgett and Pruett, 1992, Evaluation of Nitrite Production by Human Monocyte–Derived Macrophages, Biochem. and Biophys. Resch. Commun., vol. 186 (2): 775–781.

Dawson, et al., 1991, Nitric Oxide Synthase and Neuronal NADPH Diaphorase are Identical in Brain and Peripheral Tissues, Proc. Natl. Acad. Sci., vol. 88: 7797–7801.

Billiar, et al., 1990, Inducible Cytosolic Enzyme Activity for the Production of Nitrogen Oxides from L–Arginine in Hepatocytes, Biochem. and Biophys. Resch. Commun. vol. 168 (3): 1034–1040.

Billiar, et al., 1989, An L–Arginine–Dependent Mechanism Mediates Kupffer Cell Inhibition of Hepatocyte Protein Synthesis In Vitro, J. Exp. Med. 169: 1467–1472.

Ochoa, et al., 1991, Nitrogen Oxide Levels in Patients After Trauma and During Sepsis, Ann. Surg. 621–626.

Curran, et al., 1990, Multiple Cytokines are Required to Induce Hepatocyte Nitric Oxide Production and Inhibit Total Protein Synthesis, Ann. Surg., 212: 462–471.

Curran, et al., 1989, Hepatocytes Produce Nitrogen Oxides from L–Arginine in Response to Inflammatory Products of Kupffer Cells, J. Exp. Med. 170: 1769–1774.

Billiar, et al., 1990, Modulation of Nitrogen Oxide Synthesis in Vivo: $N^G$–Monomethyl–L–Arginine Inhibits Endotoxin–Induced Nitrite/Nitrate Biosynthesis While Promoting Hepatic Damage, Journ. Leukocyte Biol. 48: 565–569.

Finkel, et al., 1992, Negative Inotropic Effects of Cytokines on the Heart Mediated by Nitric Oxide, Sci. 257: 387–389.

Ochoa et al., 1992, Increased Circulating Nitrogen Oxides After Human Tumor Immunotherapy: Correlation with Toxic Hemodynamic Changes, J. Natl. Can. Instit. 864–867.

Stadler, et al., 1991, Effect of Exogenous and Endogenous Nitric Oxide on Mitochondrial Respiration of Rat Hepatocytes, Amer. Physiolo. Soc., 48: C910–C916.

Lamas, 1992, Endothelial Nitric Oxide Synthase: Molecular Cloning and Characterization of a Distinct Constitutive Enzyme Isoform, Proc. Natl. Acad. Sci., 89 (14): 6348–6352.

Leichuk, et al., 1992, Constitutive and Inducible Nitric Oxide Synthases in Human Megakaryoblastic Cells, Journ. Pharmacolo. & Exp. Therapu., 262 (3): 1220–1224.

Janssens, et al., 1992, Cloning and Expression of a cDNA Encoding Human Endothelium–Derived Relaxing Factor/Nitric Oxide Synthase, J. Biol. Chem., 267 (21): 14519–14522.

Seibert and Larrick, 1992, Competitive Reverse Transcription–Polymerase Chain Reaction (RT–PCR) Can Be Used to Obtain Quantitative Information of mRNA Levels Comparable to Traditional RNA Blot Techniques, with the Added Advantages of PCR, Nature, 359: 557–558.

Knowles, et al., 1990, Differential Induction of Brain Lung and Liver Nitric Oxide Synthase by Endotoxin in the Rat, Biochem. Journ., 270: 833–836.

Salter, et al., 1991, Widespread Tissue Distribution, Species Distribution and Changes in Activity of $Ca^2$–Dependent and $Ca^2$–Independent Nitrix Oxide Synthases, FEBS Ltrs. 291 (1): 145–149.

Springall, et al., 1992, Immunological Detection of Nitric Oxide Synthase(s) in Human Tissues Using Heterologous Antibodies Suggesting Different Isoforms, Histochem., 98 (4): 259–266.

Pfeilschifter, et al., 1992, Interleukin 1β and Tumor Necrosis Factor α Induce a Macrophage–Type of Nitric Oxide Synthase in Rat Renal Mesangial Cells, Eur. J. Biochem., 23 (1–2): 251–255.

Vanhoutte, 1992, International Symposium Smooth Muscle, Jap. J. of Pharmacol., 192P–199P.

Nakayama, et al., 1992, Cytokines and Lipopolysaccharide Induce Nitric Oxide Synthase in Cultured Rat Pulmonary Artery Smooth Muscle, Am. J. Respir. Cell Mol. Biol., 7: 471–476.

Yui, Y. et al, 1991, The Journal of Biological Chemistry, 266(19): 12544–12547.

Stuehr, D.J., et al., 1991, Proceedings of the National Academy of Sciences, U.S.A., 88(17): 7773–7777.

Lyons, C. et al., 1992, The Journal of Biological Chemistry, 267(9):6370–6374.

Evans, T. et al., 1992, Proceedings of the National Academy of Sciences, U.S.A., 89(12) 5361–5365.

Nussler, A.K., et al., 1992, Journal of Experimental Medicine, 176(1): 261–264.

White, K.A., et al., 1992, Biochemistry, 31(29): 6627–6631.

Mitchell, J.A., et al., 1992, Molecular Pharmaeology, 41(6): 1163–1168.

Oshima, H., et al., 1992, Biochemical and Biophysical Research Communications, 187(3): 1291–1297.

Iida, S., et al., 1992, The Journal of Biological Chemistry, 267(35): 25385–25388.

Hevel, J.M., et al., 1992, in *Proceedings of the International Meeting of Biology of Nitric Oxide*, Moncad, S., Editor, pp. 19–21.

Jaye et al., 1983, Nucleic Acids Research 11(8):2325–2335.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 4145 base pairs
        ( B ) TYPE: nucleic acid
        ( C ) STRANDEDNESS: double
        ( D ) TOPOLOGY: linear ( i i ) MOLECULE TYPE: cDNA
        ( A ) DESCRIPTION: Human Hepatocyte Inducible Nitric Oxide
            Synthase cDNA Clone ( i i i ) HYPOTHETICAL: NO ( i v ) ANTI-SENSE: NO ( v i ) ORIGINAL SOURCE:
        ( F ) TISSUE TYPE: Induced Human Hepatocyte RNA ( v i i ) IMMEDIATE SOURCE:
        ( A ) LIBRARY: Lambda Zap II cDNA
        ( B ) CLONE: pHINOS ( v i i i ) POSITION IN GENOME:
        ( A ) CHROMOSOME/SEGMENT: unknown
        ( B ) MAP POSITION: unknown
        ( C ) UNITS: unknown ( i x ) FEATURE:
        ( A ) NAME/KEY: CDS
        ( B ) LOCATION: 207..3668
        ( C ) IDENTIFICATION METHOD: Experiment ( x i ) SEQUENCE DESCRIPTION: SEQ ID NO:1:

```
CTGCTTTAAA  ATCTCTCGGC  CACCTTTGAT  GAGGGGACTG  GGCAGTTCTA  GACAGTCCCG        60

AAGTTCTCAA  GGCACAGGTC  TCTTCCTGGT  TTGACTGTCC  TTACCCCGGG  GAGGCAGTGC       120

AGCCAGCTGC  AAGCCCCACA  GTGAAGAACA  TCTGAGCTCA  AATCCAGATA  AGTGACATAA       180

GTGACCTGCT  TTGTAAAGCC  ATAGAG ATG GCC TGT CCT TGG AAA TTT CTG TTC           233
                              Met Ala Cys Pro Trp Lys Phe Leu Phe
                               1               5

AAG ACC AAA TTC CAC CAG TAT GCA ATG AAT GGG GAA AAA GAC ATC AAC             281
Lys Thr Lys Phe His Gln Tyr Ala Met Asn Gly Glu Lys Asp Ile Asn
 10              15                  20              25

AAC AAT GTG GAG AAA GCC CCC TGT GCC ACC TCC AGT CCA GTG ACA CAG             329
Asn Asn Val Glu Lys Ala Pro Cys Ala Thr Ser Ser Pro Val Thr Gln
                 30              35                  40

GAT GAC CTT CAG TAT CAC AAC CTC AGC AAG CAG CAG AAT GAG TCC CCG             377
Asp Asp Leu Gln Tyr His Asn Leu Ser Lys Gln Gln Asn Glu Ser Pro
             45                  50                  55

CAG CCC CTC GTG GAG ACG GGA AAG AAG TCT CCA GAA TCT CTG GTC AAG             425
Gln Pro Leu Val Glu Thr Gly Lys Lys Ser Pro Glu Ser Leu Val Lys
         60                  65                  70

CTG GAT GCA ACC CCA TTG TCC TCC CCA CGG CAT GTG AGG ATC AAA AAC             473
Leu Asp Ala Thr Pro Leu Ser Ser Pro Arg His Val Arg Ile Lys Asn
     75                  80                  85

TGG GGC AGC GGG ATG ACT TTC CAA GAC ACA CTT CAC CAT AAG GCC AAA             521
Trp Gly Ser Gly Met Thr Phe Gln Asp Thr Leu His His Lys Ala Lys
 90              95                 100                 105

GGG ATT TTA ACT TGC AGG TCC AAA TCT TGC CTG GGG TCC ATT ATG ACT             569
Gly Ile Leu Thr Cys Arg Ser Lys Ser Cys Leu Gly Ser Ile Met Thr
                110                 115                 120
```

-continued

| | | | | | | | | | | | | | | | |
|---|---|---|---|---|---|---|---|---|---|---|---|---|---|---|---|
| CCC | AAA | AGT | TTG | ACC | AGA | GGA | CCC | AGG | GAC | AAG | CCT | ACC | CCT | CCA | GAT | 617 |
| Pro | Lys | Ser | Leu | Thr | Arg | Gly | Pro | Arg | Asp | Lys | Pro | Thr | Pro | Pro | Asp | |
| | | | 125 | | | | 130 | | | | | | 135 | | | |
| GAG | CTT | CTA | CCT | CAA | GCT | ATC | GAA | TTT | GTC | AAC | CAA | TAT | TAC | GGC | TCC | 665 |
| Glu | Leu | Leu | Pro | Gln | Ala | Ile | Glu | Phe | Val | Asn | Gln | Tyr | Tyr | Gly | Ser | |
| | | | | 140 | | | | | 145 | | | | | 150 | | |
| TTC | AAA | GAG | GCA | AAA | ATA | GAG | GAA | CAT | CTG | GCC | AGG | GTG | GAA | GCG | GTA | 713 |
| Phe | Lys | Glu | Ala | Lys | Ile | Glu | Glu | His | Leu | Ala | Arg | Val | Glu | Ala | Val | |
| | 155 | | | | | 160 | | | | | 165 | | | | | |
| ACA | AAG | GAG | ATA | GAA | ACA | ACA | GGA | ACC | TAC | CAA | CTG | ACG | GGA | GAT | GAG | 761 |
| Thr | Lys | Glu | Ile | Glu | Thr | Thr | Gly | Thr | Tyr | Gln | Leu | Thr | Gly | Asp | Glu | |
| 170 | | | | | 175 | | | | | 180 | | | | | 185 | |
| CTC | ATC | TTC | GCC | ACC | AAG | CAG | GCC | TGG | CGC | AAT | GCC | CCA | CGC | TGC | ATT | 809 |
| Leu | Ile | Phe | Ala | Thr | Lys | Gln | Ala | Trp | Arg | Asn | Ala | Pro | Arg | Cys | Ile | |
| | | | | 190 | | | | | 195 | | | | | 200 | | |
| GGG | AGG | ATC | CAG | TGG | TCC | AAC | CTG | CAG | GTC | TTC | GAT | GCC | CGC | AGC | TGT | 857 |
| Gly | Arg | Ile | Gln | Trp | Ser | Asn | Leu | Gln | Val | Phe | Asp | Ala | Arg | Ser | Cys | |
| | | | 205 | | | | 210 | | | | | 215 | | | | |
| TCC | ACT | GCC | CGG | GAA | ATG | TTT | GAA | CAC | ATC | TGC | AGA | CAC | GTG | CGT | TAC | 905 |
| Ser | Thr | Ala | Arg | Glu | Met | Phe | Glu | His | Ile | Cys | Arg | His | Val | Arg | Tyr | |
| | | 220 | | | | | 225 | | | | | 230 | | | | |
| TCC | ACC | AAC | AAT | GGC | AAC | ATC | AGG | TCG | GCC | ATC | ACC | GTG | TTC | CCC | CAG | 953 |
| Ser | Thr | Asn | Asn | Gly | Asn | Ile | Arg | Ser | Ala | Ile | Thr | Val | Phe | Pro | Gln | |
| | 235 | | | | | 240 | | | | | 245 | | | | | |
| CGG | AGT | GAT | GGC | AAG | CAC | GAC | TTC | CGG | GTG | TGG | AAT | GCT | CAG | CTC | ATC | 1001 |
| Arg | Ser | Asp | Gly | Lys | His | Asp | Phe | Arg | Val | Trp | Asn | Ala | Gln | Leu | Ile | |
| 250 | | | | | 255 | | | | | 260 | | | | | 265 | |
| CGC | TAT | GCT | GGC | TAC | CAG | ATG | CCA | GAT | GGC | AGC | ATC | AGA | GGG | GAC | CCT | 1049 |
| Arg | Tyr | Ala | Gly | Tyr | Gln | Met | Pro | Asp | Gly | Ser | Ile | Arg | Gly | Asp | Pro | |
| | | | | 270 | | | | | 275 | | | | | 280 | | |
| GCC | AAC | GTG | GAA | TTC | ACT | CAG | CTG | TGC | ATC | GAC | CTG | GGC | TGG | AAG | CCC | 1097 |
| Ala | Asn | Val | Glu | Phe | Thr | Gln | Leu | Cys | Ile | Asp | Leu | Gly | Trp | Lys | Pro | |
| | | | 285 | | | | | 290 | | | | | 295 | | | |
| AAG | TAC | GGC | CGC | TTC | GAT | GTG | GTC | CCC | CTG | GTC | CTG | CAG | GCC | AAT | GGC | 1145 |
| Lys | Tyr | Gly | Arg | Phe | Asp | Val | Val | Pro | Leu | Val | Leu | Gln | Ala | Asn | Gly | |
| | | 300 | | | | | 305 | | | | | 310 | | | | |
| CGT | GAC | CCT | GAG | CTC | TTC | GAA | ATC | CCA | CCT | GAC | CTT | GTG | CTT | GAG | GTG | 1193 |
| Arg | Asp | Pro | Glu | Leu | Phe | Glu | Ile | Pro | Pro | Asp | Leu | Val | Leu | Glu | Val | |
| | 315 | | | | | 320 | | | | | 325 | | | | | |
| GCC | ATG | GAA | CAT | CCC | AAA | TAC | GAG | TGG | TTT | CGG | GAA | CTG | GAG | CTA | AAG | 1241 |
| Ala | Met | Glu | His | Pro | Lys | Tyr | Glu | Trp | Phe | Arg | Glu | Leu | Glu | Leu | Lys | |
| 330 | | | | | 335 | | | | | 340 | | | | | 345 | |
| TGG | TAC | GCC | CTG | CCT | GCA | GTG | GCC | AAC | ATG | CTG | CTT | GAG | GTG | GGC | GGC | 1289 |
| Trp | Tyr | Ala | Leu | Pro | Ala | Val | Ala | Asn | Met | Leu | Leu | Glu | Val | Gly | Gly | |
| | | | | 350 | | | | | 355 | | | | | 360 | | |
| CTG | GAG | TTC | CCA | GGG | TGC | CCC | TTC | AAT | GGC | TGG | TAC | ATG | GGC | ACA | GAG | 1337 |
| Leu | Glu | Phe | Pro | Gly | Cys | Pro | Phe | Asn | Gly | Trp | Tyr | Met | Gly | Thr | Glu | |
| | | | 365 | | | | | 370 | | | | | 375 | | | |
| ATC | GGA | GTC | CGG | GAC | TTC | TGT | GAC | GTC | CAG | CGC | TAC | AAC | ATC | CTG | GAG | 1385 |
| Ile | Gly | Val | Arg | Asp | Phe | Cys | Asp | Val | Gln | Arg | Tyr | Asn | Ile | Leu | Glu | |
| | | 380 | | | | | 385 | | | | | 390 | | | | |
| GAA | GTG | GGC | AGG | AGA | ATG | GGC | CTG | GAA | ACG | CAC | AAG | CTG | GCC | TCG | CTC | 1433 |
| Glu | Val | Gly | Arg | Arg | Met | Gly | Leu | Glu | Thr | His | Lys | Leu | Ala | Ser | Leu | |
| | 395 | | | | | 400 | | | | | 405 | | | | | |
| TGG | AAA | GAC | CAG | GCT | GTC | GTT | GAG | ATC | AAC | ATT | GCT | GTG | ATC | CAT | AGT | 1481 |
| Trp | Lys | Asp | Gln | Ala | Val | Val | Glu | Ile | Asn | Ile | Ala | Val | Ile | His | Ser | |
| 410 | | | | 415 | | | | | 420 | | | | | 425 | | |
| TTT | CAG | AAG | CAG | AAT | GTG | ACC | ATC | ATG | GAC | CAC | CAC | TCG | GCT | GCA | GAA | 1529 |
| Phe | Gln | Lys | Gln | Asn | Val | Thr | Ile | Met | Asp | His | His | Ser | Ala | Ala | Glu | |
| | | | | 430 | | | | | 435 | | | | | 440 | | |

| | | | | | | | | | | | | | | | | |
|---|---|---|---|---|---|---|---|---|---|---|---|---|---|---|---|---|
| TCC | TTC | ATG | AAG | TAC | ATG | CAG | AAT | GAA | TAC | CGG | TCC | CGT | GGG | GGC | TGC | 1577 |
| Ser | Phe | Met | Lys 445 | Tyr | Met | Gln | Asn | Glu 450 | Tyr | Arg | Ser | Arg | Gly 455 | Gly | Cys | |
| CCG | GCA | GAC | TGG | ATT | TGG | CTG | GTC | CCT | CCC | ATG | TCT | GGG | AGC | ATC | ACC | 1625 |
| Pro | Ala | Asp 460 | Trp | Ile | Trp | Leu | Val | Pro 465 | Pro | Met | Ser | Gly 470 | Ser | Ile | Thr | |
| CCC | GTG | TTT | CAC | CAG | GAG | ATG | CTG | AAC | TAC | GTC | CTG | TCC | CCT | TTC | TAC | 1673 |
| Pro | Val 475 | Phe | His | Gln | Glu | Met 480 | Leu | Asn | Tyr | Val | Leu 485 | Ser | Pro | Phe | Tyr | |
| TAC | TAT | CAG | GTA | GAG | GCC | TGG | AAA | ACC | CAT | GTC | TGG | CAG | GAC | GAG | AAG | 1721 |
| Tyr 490 | Tyr | Gln | Val | Glu | Ala 495 | Trp | Lys | Thr | His | Val 500 | Trp | Gln | Asp | Glu | Lys 505 | |
| CGG | AGA | CCC | AAG | AGA | AGA | GAG | ATT | CCA | TTG | AAA | GTC | TTG | GTC | AAA | GCT | 1769 |
| Arg | Arg | Pro | Lys 510 | Arg | Arg | Glu | Ile | Pro 515 | Leu | Lys | Val | Leu | Val 520 | Lys | Ala | |
| GTG | CTC | TTT | GCC | TGT | ATG | CTG | ATG | CGC | AAG | ACA | ATG | GCG | TCC | CGA | GTC | 1817 |
| Val | Leu | Phe | Ala 525 | Cys | Met | Leu | Met | Arg 530 | Lys | Thr | Met | Ala | Ser 535 | Arg | Val | |
| AGA | GTC | ACC | ATC | CTC | TTT | GCG | ACA | GAG | ACA | GGA | AAA | TCA | GAG | GCG | CTG | 1865 |
| Arg | Val | Thr 540 | Ile | Leu | Phe | Ala | Thr 545 | Glu | Thr | Gly | Lys | Ser 550 | Glu | Ala | Leu | |
| GCC | TGG | GAC | CTG | GGG | GCC | TTA | TTC | AGC | TGT | GCC | TTC | AAC | CCC | AAG | GTT | 1913 |
| Ala | Trp 555 | Asp | Leu | Gly | Ala | Leu 560 | Phe | Ser | Cys | Ala | Phe 565 | Asn | Pro | Lys | Val | |
| GTC | TGC | ATG | GAT | AAG | TAC | AGG | CTG | AGC | TGC | CTG | GAG | GAG | GAA | CGG | CTG | 1961 |
| Val 570 | Cys | Met | Asp | Lys | Tyr 575 | Arg | Leu | Ser | Cys | Leu 580 | Glu | Glu | Glu | Arg | Leu 585 | |
| CTG | TTG | GTG | GTG | ACC | AGT | ACG | TTT | GGC | AAT | GGA | GAC | TGC | CCT | GGC | AAT | 2009 |
| Leu | Leu | Val | Val | Thr 590 | Ser | Thr | Phe | Gly | Asn 595 | Gly | Asp | Cys | Pro | Gly 600 | Asn | |
| GGA | GAG | AAA | CTG | AAG | AAA | TCG | CTC | TTC | ATG | CTG | AAA | GAG | CTC | AAC | AAC | 2057 |
| Gly | Glu | Lys | Leu 605 | Lys | Lys | Ser | Leu | Phe 610 | Met | Leu | Lys | Glu | Leu 615 | Asn | Asn | |
| AAA | TTC | AGG | TAC | GCT | GTG | TTT | GGC | CTC | GGC | TCC | AGC | ATG | TAC | CCT | CGG | 2105 |
| Lys | Phe | Arg 620 | Tyr | Ala | Val | Phe | Gly 625 | Leu | Gly | Ser | Ser | Met 630 | Tyr | Pro | Arg | |
| TTC | TGC | GCC | TTT | GCT | CAT | GAC | ATT | GAT | CAG | AAG | CTG | TCC | CAC | CTG | GGG | 2153 |
| Phe | Cys 635 | Ala | Phe | Ala | His | Asp 640 | Ile | Asp | Gln | Lys | Leu 645 | Ser | His | Leu | Gly | |
| GCC | TCT | CAG | CTC | ACC | CCG | ATG | GGA | GAA | GGG | GAT | GAG | CTC | AGT | GGG | CAG | 2201 |
| Ala 650 | Ser | Gln | Leu | Thr | Pro 655 | Met | Gly | Glu | Gly | Asp 660 | Glu | Leu | Ser | Gly | Gln 665 | |
| GAG | GAC | GCC | TTC | CGC | AGC | TGG | GCC | GTG | CAA | ACC | TTC | AAG | GCA | GCC | TGT | 2249 |
| Glu | Asp | Ala | Phe | Arg 670 | Ser | Trp | Ala | Val | Gln 675 | Thr | Phe | Lys | Ala | Ala 680 | Cys | |
| GAG | ACG | TTT | GAT | GTC | CGA | GGC | AAA | CAG | CAC | ATT | CAG | ATC | CCC | AAG | CTC | 2297 |
| Glu | Thr | Phe | Asp 685 | Val | Arg | Gly | Lys | Gln 690 | His | Ile | Gln | Ile | Pro 695 | Lys | Leu | |
| TAC | ACC | TCC | AAT | GTG | ACC | TGG | GAC | CCG | CAC | CAC | TAC | AGG | CTC | GTG | CAG | 2345 |
| Tyr | Thr | Ser 700 | Asn | Val | Thr | Trp | Asp 705 | Pro | His | His | Tyr | Arg 710 | Leu | Val | Gln | |
| GAC | TCA | CAG | CCT | TTG | GAC | CTC | AGC | AAA | GCC | CTC | AGC | AGC | ATG | CAT | GCC | 2393 |
| Asp | Ser | Gln 715 | Pro | Leu | Asp | Leu | Ser 720 | Lys | Ala | Leu | Ser | Ser 725 | Met | His | Ala | |
| AAG | AAC | GTG | TTC | ACC | ATG | AGG | CTC | AAA | TCT | CGG | CAG | AAT | CTA | CAA | AGT | 2441 |
| Lys 730 | Asn | Val | Phe | Thr | Met 735 | Arg | Leu | Lys | Ser | Arg 740 | Gln | Asn | Leu | Gln | Ser 745 | |
| CCG | ACA | TCC | AGC | CGT | GCC | ACC | ATC | CTG | GTG | GAA | CTC | TCC | TGT | GAG | GAT | 2489 |
| Pro | Thr | Ser | Ser | Arg 750 | Ala | Thr | Ile | Leu | Val 755 | Glu | Leu | Ser | Cys | Glu 760 | Asp | |

```
GGC  CAA  GGC  CTG  AAC  TAC  CTG  CCG  GGG  GAG  CAC  CTT  GGG  GTT  TGC  CCA              2537
Gly  Gln  Gly  Leu  Asn  Tyr  Leu  Pro  Gly  Glu  His  Leu  Gly  Val  Cys  Pro
               765                      770                      775

GGC  AAC  CAG  CCG  GCC  CTG  GTC  CAA  GGC  ATC  CTG  GAG  CGA  GTG  GTG  GAT              2585
Gly  Asn  Gln  Pro  Ala  Leu  Val  Gln  Gly  Ile  Leu  Glu  Arg  Val  Val  Asp
               780                      785                      790

GGC  CCC  ACA  CCC  CAC  CAG  ACA  GTG  CGC  CTG  GAG  GAC  CTG  GAT  GAG  AGT              2633
Gly  Pro  Thr  Pro  His  Gln  Thr  Val  Arg  Leu  Glu  Asp  Leu  Asp  Glu  Ser
     795                      800                      805

GGC  AGC  TAC  TGG  GTC  AGT  GAC  AAG  AGG  CTG  CCC  CCC  TGC  TCA  CTC  AGC              2681
Gly  Ser  Tyr  Trp  Val  Ser  Asp  Lys  Arg  Leu  Pro  Pro  Cys  Ser  Leu  Ser
810                      815                      820                      825

CAG  GCC  CTC  ACC  TAC  TCC  CCG  GAC  ATC  ACC  ACA  CCC  CCA  ACC  CAG  CTG              2729
Gln  Ala  Leu  Thr  Tyr  Ser  Pro  Asp  Ile  Thr  Thr  Pro  Pro  Thr  Gln  Leu
               830                      835                      840

CTG  CTC  CAA  AAG  CTG  GCC  CAG  GTG  GCC  ACA  GAA  GAG  CCT  GAG  AGA  CAG              2777
Leu  Leu  Gln  Lys  Leu  Ala  Gln  Val  Ala  Thr  Glu  Glu  Pro  Glu  Arg  Gln
               845                      850                      855

AGG  CTG  GAG  GCC  CTG  TGC  CAG  CCC  TCA  GAG  TAC  AGC  AAG  TGG  AAG  TTC              2825
Arg  Leu  Glu  Ala  Leu  Cys  Gln  Pro  Ser  Glu  Tyr  Ser  Lys  Trp  Lys  Phe
               860                      865                      870

ACC  AAC  AGC  CCC  ACA  TTC  CTG  GAG  GTG  CTA  GAG  GAG  TTC  CCG  TCC  CTG              2873
Thr  Asn  Ser  Pro  Thr  Phe  Leu  Glu  Val  Leu  Glu  Glu  Phe  Pro  Ser  Leu
     875                      880                      885

CGG  GTG  TCT  GCT  GGC  TTC  CTG  CTT  TCC  CAG  CTC  CCC  ATT  CTG  AAG  CCC              2921
Arg  Val  Ser  Ala  Gly  Phe  Leu  Leu  Ser  Gln  Leu  Pro  Ile  Leu  Lys  Pro
890                      895                      900                      905

AGG  TTC  TAC  TCC  ATC  AGC  TCC  TCC  CGG  GAT  CAC  ACG  CCC  ACG  GAG  ATC              2969
Arg  Phe  Tyr  Ser  Ile  Ser  Ser  Ser  Arg  Asp  His  Thr  Pro  Thr  Glu  Ile
               910                      915                      920

CAC  CTG  ACT  GTG  GCC  GTG  GTC  ACC  TAC  CAC  ACC  GGA  GAT  GGC  CAG  GGT              3017
His  Leu  Thr  Val  Ala  Val  Val  Thr  Tyr  His  Thr  Gly  Asp  Gly  Gln  Gly
               925                      930                      935

CCC  CTG  CAC  CAC  GGT  GTC  TGC  AGC  ACA  TGG  CTC  AAC  AGC  CTG  AAG  CCC              3065
Pro  Leu  His  His  Gly  Val  Cys  Ser  Thr  Trp  Leu  Asn  Ser  Leu  Lys  Pro
     940                      945                      950

CAA  GAC  CCA  GTG  CCC  TGC  TTT  GTG  CGG  AAT  GCC  AGC  GCC  TTC  CAC  CTC              3113
Gln  Asp  Pro  Val  Pro  Cys  Phe  Val  Arg  Asn  Ala  Ser  Ala  Phe  His  Leu
955                      960                      965

CCC  GAG  GAT  CCC  TCC  CAT  CCT  TGC  ATC  CTC  ATC  GGG  CCT  GGC  ACA  GGC              3161
Pro  Glu  Asp  Pro  Ser  His  Pro  Cys  Ile  Leu  Ile  Gly  Pro  Gly  Thr  Gly
970                      975                      980                      985

ATC  GTG  CCC  TTC  CGC  AGT  TTC  TGG  CAG  CAA  CGG  CTC  CAT  GAC  TCC  CAG              3209
Ile  Val  Pro  Phe  Arg  Ser  Phe  Trp  Gln  Gln  Arg  Leu  His  Asp  Ser  Gln
               990                      995                      1000

CAC  AAG  GGA  GTG  CGG  GGA  GGC  CGC  ATG  ACC  TTG  GTG  TTT  GGG  TGC  CGC              3257
His  Lys  Gly  Val  Arg  Gly  Gly  Arg  Met  Thr  Leu  Val  Phe  Gly  Cys  Arg
               1005                     1010                     1015

CGC  CCA  GAT  GAG  GAC  CAC  ATC  TAC  CAG  GAG  GAG  ATG  CTG  GAG  ATG  GCC              3305
Arg  Pro  Asp  Glu  Asp  His  Ile  Tyr  Gln  Glu  Glu  Met  Leu  Glu  Met  Ala
               1020                     1025                     1030

CAG  AAG  GGG  GTG  CTG  CAT  GCG  GTG  CAC  ACA  GCC  TAT  TCC  CGC  CTG  CCT              3353
Gln  Lys  Gly  Val  Leu  His  Ala  Val  His  Thr  Ala  Tyr  Ser  Arg  Leu  Pro
               1035                     1040                     1045

GGC  AAG  CCC  AAG  GTC  TAT  GTT  CAG  GAC  ATC  CTG  CGG  CAG  CAG  CTG  GCC              3401
Gly  Lys  Pro  Lys  Val  Tyr  Val  Gln  Asp  Ile  Leu  Arg  Gln  Gln  Leu  Ala
1050                     1055                     1060                     1065

AGC  GAG  GTG  CTC  CGT  GTG  CTC  CAC  AAG  GAG  CCA  GGC  CAC  CTC  TAT  GTT              3449
Ser  Glu  Val  Leu  Arg  Val  Leu  His  Lys  Glu  Pro  Gly  His  Leu  Tyr  Val
               1070                     1075                     1080
```

| | | | | | | | | | | | | | | | | |
|---|---|---|---|---|---|---|---|---|---|---|---|---|---|---|---|---|
| TGC | GGG | GAT | GTG | CGC | ATG | GCC | CGG | GAC | GTG | GCC | CAC | ACC | CTG | AAG | CAG | 3497 |
| Cys | Gly | Asp | Val | Arg | Met | Ala | Arg | Asp | Val | Ala | His | Thr | Leu | Lys | Gln | |
| | | 1085 | | | | | 1090 | | | | | 1095 | | | | |
| CTG | GTG | GCT | GCC | AAG | CTG | AAA | TTG | AAT | GAG | GAG | CAG | GTC | GAG | GAC | TAT | 3545 |
| Leu | Val | Ala | Ala | Lys | Leu | Lys | Leu | Asn | Glu | Glu | Gln | Val | Glu | Asp | Tyr | |
| | 1100 | | | | | 1105 | | | | | 1110 | | | | | |
| TTC | TTT | CAG | CTC | AAG | AGC | CAG | AAG | CGC | TAT | CAC | GAA | GAT | ATC | TTC | GGT | 3593 |
| Phe | Phe | Gln | Leu | Lys | Ser | Gln | Lys | Arg | Tyr | His | Glu | Asp | Ile | Phe | Gly | |
| | 1115 | | | | | 1120 | | | | | 1125 | | | | | |
| GCT | GTA | TTT | CCT | TAC | GAG | GCG | AAG | AAG | GAC | AGG | GTG | GCG | GTG | CAG | CCC | 3641 |
| Ala | Val | Phe | Pro | Tyr | Glu | Ala | Lys | Lys | Asp | Arg | Val | Ala | Val | Gln | Pro | |
| 1130 | | | | 1135 | | | | | 1140 | | | | | 1145 | | |
| AGC | AGC | CTG | GAG | ATG | TCA | GCG | CTC | TGAGGGCCTA | | CAGGAGGGGT | | TAAAGCTGCC | | | | 3695 |
| Ser | Ser | Leu | Glu | Met | Ser | Ala | Leu | | | | | | | | | |
| | | | | 1150 | | | | | | | | | | | | |

| | | | | |
|---|---|---|---|---|
| GGCACAGAAC | TTAAGGATGG | AGCCAGCTCT | GCATTATCTG | AGGTCACAGG | GCCTGGGGAG | 3755 |
| ATGGAGGAAA | GTGATATCCC | CCAGCCTCAA | GTCTTATTTC | CTCAACGTTG | CTCCCCATCA | 3815 |
| AGCCCTTTAC | TTGACCTCCT | AACAAGTAGC | ACCCTGGATT | GATCGGAGCC | TCCTCTCTCA | 3875 |
| AACTGGGGCC | TCCCTGGTCC | CTTGGAGACA | AAATCTTAAA | TGCCAGGCCT | GGCGAGTGGG | 3935 |
| TGAAAGATGG | AACTTGCTGC | TGAGTGCACC | ACTTCAAGTG | ACCACCAGGA | GGTGCTATCG | 3995 |
| CACCACTGTG | TATTTAACTG | CCTTGTGTAC | AGTTATTTAT | GCCTCTGTAT | TTAAAAAACT | 4055 |
| AACACCCAGT | CTGTTCCCCA | TGGCCACTTG | GGTCTTCCCT | GTATGATTCC | TTGATGGAGA | 4115 |
| TATTTACATG | AATTGCATTT | TACTTTAATC | | | | 4145 |

(2) INFORMATION FOR SEQ ID NO:2:

(i) SEQUENCE CHARACTERISTICS:
        (A) LENGTH: 1153 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Cys Pro Trp Lys Phe Leu Phe Lys Thr Lys Phe His Gln Tyr
  1               5                  10                  15

Ala Met Asn Gly Glu Lys Asp Ile Asn Asn Val Glu Lys Ala Pro
             20                  25                  30

Cys Ala Thr Ser Ser Pro Val Thr Gln Asp Asp Leu Gln Tyr His Asn
             35                  40                  45

Leu Ser Lys Gln Gln Asn Glu Ser Pro Gln Pro Leu Val Glu Thr Gly
         50                  55                  60

Lys Lys Ser Pro Glu Ser Leu Val Lys Leu Asp Ala Thr Pro Leu Ser
 65                  70                  75                  80

Ser Pro Arg His Val Arg Ile Lys Asn Trp Gly Ser Gly Met Thr Phe
                 85                  90                  95

Gln Asp Thr Leu His His Lys Ala Lys Gly Ile Leu Thr Cys Arg Ser
                100                 105                 110

Lys Ser Cys Leu Gly Ser Ile Met Thr Pro Lys Ser Leu Thr Arg Gly
            115                 120                 125

Pro Arg Asp Lys Pro Thr Pro Asp Glu Leu Leu Pro Gln Ala Ile
        130                 135                 140

Glu Phe Val Asn Gln Tyr Tyr Gly Ser Phe Lys Glu Ala Lys Ile Glu
145                 150                 155                 160

Glu His Leu Ala Arg Val Glu Ala Val Thr Lys Glu Ile Glu Thr Thr
```

|     |     |     |     | 165 |     |     |     | 170 |     |     |     | 175 |     |
| --- | --- | --- | --- | --- | --- | --- | --- | --- | --- | --- | --- | --- | --- |
| Gly | Thr | Tyr | Gln | Leu | Thr | Gly | Asp | Glu | Leu | Ile | Phe | Ala | Thr | Lys | Gln |
|     |     |     | 180 |     |     |     |     | 185 |     |     |     |     | 190 |
| Ala | Trp | Arg | Asn | Ala | Pro | Arg | Cys | Ile | Gly | Arg | Ile | Gln | Trp | Ser | Asn |
|     |     |     | 195 |     |     |     |     | 200 |     |     |     |     | 205 |
| Leu | Gln | Val | Phe | Asp | Ala | Arg | Ser | Cys | Ser | Thr | Ala | Arg | Glu | Met | Phe |
|     |     | 210 |     |     |     |     | 215 |     |     |     |     | 220 |
| Glu | His | Ile | Cys | Arg | His | Val | Arg | Tyr | Ser | Thr | Asn | Asn | Gly | Asn | Ile |
| 225 |     |     |     |     | 230 |     |     |     |     | 235 |     |     |     |     | 240 |
| Arg | Ser | Ala | Ile | Thr | Val | Phe | Pro | Gln | Arg | Ser | Asp | Gly | Lys | His | Asp |
|     |     |     |     | 245 |     |     |     |     | 250 |     |     |     |     | 255 |
| Phe | Arg | Val | Trp | Asn | Ala | Gln | Leu | Ile | Arg | Tyr | Ala | Gly | Tyr | Gln | Met |
|     |     |     | 260 |     |     |     |     | 265 |     |     |     |     | 270 |
| Pro | Asp | Gly | Ser | Ile | Arg | Gly | Asp | Pro | Ala | Asn | Val | Glu | Phe | Thr | Gln |
|     |     | 275 |     |     |     |     | 280 |     |     |     |     | 285 |
| Leu | Cys | Ile | Asp | Leu | Gly | Trp | Lys | Pro | Lys | Tyr | Gly | Arg | Phe | Asp | Val |
|     | 290 |     |     |     |     | 295 |     |     |     |     | 300 |
| Val | Pro | Leu | Val | Leu | Gln | Ala | Asn | Gly | Arg | Asp | Pro | Glu | Leu | Phe | Glu |
| 305 |     |     |     |     | 310 |     |     |     |     | 315 |     |     |     |     | 320 |
| Ile | Pro | Pro | Asp | Leu | Val | Leu | Glu | Val | Ala | Met | Glu | His | Pro | Lys | Tyr |
|     |     |     |     | 325 |     |     |     |     | 330 |     |     |     |     | 335 |
| Glu | Trp | Phe | Arg | Glu | Leu | Glu | Leu | Lys | Trp | Tyr | Ala | Leu | Pro | Ala | Val |
|     |     |     | 340 |     |     |     |     | 345 |     |     |     |     | 350 |
| Ala | Asn | Met | Leu | Leu | Glu | Val | Gly | Gly | Leu | Glu | Phe | Pro | Gly | Cys | Pro |
|     |     | 355 |     |     |     |     | 360 |     |     |     |     | 365 |
| Phe | Asn | Gly | Trp | Tyr | Met | Gly | Thr | Glu | Ile | Gly | Val | Arg | Asp | Phe | Cys |
|     | 370 |     |     |     |     | 375 |     |     |     |     | 380 |
| Asp | Val | Gln | Arg | Tyr | Asn | Ile | Leu | Glu | Glu | Val | Gly | Arg | Arg | Met | Gly |
| 385 |     |     |     |     | 390 |     |     |     |     | 395 |     |     |     |     | 400 |
| Leu | Glu | Thr | His | Lys | Leu | Ala | Ser | Leu | Trp | Lys | Asp | Gln | Ala | Val | Val |
|     |     |     |     | 405 |     |     |     |     | 410 |     |     |     |     | 415 |
| Glu | Ile | Asn | Ile | Ala | Val | Ile | His | Ser | Phe | Gln | Lys | Gln | Asn | Val | Thr |
|     |     |     | 420 |     |     |     |     | 425 |     |     |     |     | 430 |
| Ile | Met | Asp | His | His | Ser | Ala | Ala | Glu | Ser | Phe | Met | Lys | Tyr | Met | Gln |
|     |     | 435 |     |     |     |     | 440 |     |     |     |     | 445 |
| Asn | Glu | Tyr | Arg | Ser | Arg | Gly | Gly | Cys | Pro | Ala | Asp | Trp | Ile | Trp | Leu |
|     | 450 |     |     |     |     | 455 |     |     |     |     | 460 |
| Val | Pro | Pro | Met | Ser | Gly | Ser | Ile | Thr | Pro | Val | Phe | His | Gln | Glu | Met |
| 465 |     |     |     |     | 470 |     |     |     |     | 475 |     |     |     |     | 480 |
| Leu | Asn | Tyr | Val | Leu | Ser | Pro | Phe | Tyr | Tyr | Tyr | Gln | Val | Glu | Ala | Trp |
|     |     |     |     | 485 |     |     |     |     | 490 |     |     |     |     | 495 |
| Lys | Thr | His | Val | Trp | Gln | Asp | Glu | Lys | Arg | Arg | Pro | Lys | Arg | Arg | Glu |
|     |     |     | 500 |     |     |     |     | 505 |     |     |     |     | 510 |
| Ile | Pro | Leu | Lys | Val | Leu | Val | Lys | Ala | Val | Leu | Phe | Ala | Cys | Met | Leu |
|     |     | 515 |     |     |     |     | 520 |     |     |     |     | 525 |
| Met | Arg | Lys | Thr | Met | Ala | Ser | Arg | Val | Arg | Val | Thr | Ile | Leu | Phe | Ala |
|     | 530 |     |     |     |     | 535 |     |     |     |     | 540 |
| Thr | Glu | Thr | Gly | Lys | Ser | Glu | Ala | Leu | Ala | Trp | Asp | Leu | Gly | Ala | Leu |
| 545 |     |     |     |     | 550 |     |     |     |     | 555 |     |     |     |     | 560 |
| Phe | Ser | Cys | Ala | Phe | Asn | Pro | Lys | Val | Val | Cys | Met | Asp | Lys | Tyr | Arg |
|     |     |     |     | 565 |     |     |     |     | 570 |     |     |     |     | 575 |
| Leu | Ser | Cys | Leu | Glu | Glu | Glu | Arg | Leu | Leu | Leu | Val | Val | Thr | Ser | Thr |
|     |     |     | 580 |     |     |     |     | 585 |     |     |     |     | 590 |

-continued

```
Phe  Gly  Asn  Gly  Asp  Cys  Pro  Gly  Asn  Gly  Glu  Lys  Leu  Lys  Lys  Ser
          595                      600                     605

Leu  Phe  Met  Leu  Lys  Glu  Leu  Asn  Asn  Lys  Phe  Arg  Tyr  Ala  Val  Phe
610                           615                     620

Gly  Leu  Gly  Ser  Ser  Met  Tyr  Pro  Arg  Phe  Cys  Ala  Phe  Ala  His  Asp
625                      630                     635                          640

Ile  Asp  Gln  Lys  Leu  Ser  His  Leu  Gly  Ala  Ser  Gln  Leu  Thr  Pro  Met
                    645                     650                          655

Gly  Glu  Gly  Asp  Glu  Leu  Ser  Gly  Gln  Glu  Asp  Ala  Phe  Arg  Ser  Trp
                    660                     665                     670

Ala  Val  Gln  Thr  Phe  Lys  Ala  Ala  Cys  Glu  Thr  Phe  Asp  Val  Arg  Gly
               675                     680                     685

Lys  Gln  His  Ile  Gln  Ile  Pro  Lys  Leu  Tyr  Thr  Ser  Asn  Val  Thr  Trp
     690                     695                     700

Asp  Pro  His  His  Tyr  Arg  Leu  Val  Gln  Asp  Ser  Gln  Pro  Leu  Asp  Leu
705                      710                     715                          720

Ser  Lys  Ala  Leu  Ser  Ser  Met  His  Ala  Lys  Asn  Val  Phe  Thr  Met  Arg
                    725                     730                          735

Leu  Lys  Ser  Arg  Gln  Asn  Leu  Gln  Ser  Pro  Thr  Ser  Ser  Arg  Ala  Thr
               740                     745                     750

Ile  Leu  Val  Glu  Leu  Ser  Cys  Glu  Asp  Gly  Gln  Gly  Leu  Asn  Tyr  Leu
          755                     760                     765

Pro  Gly  Glu  His  Leu  Gly  Val  Cys  Pro  Gly  Asn  Gln  Pro  Ala  Leu  Val
     770                     775                     780

Gln  Gly  Ile  Leu  Glu  Arg  Val  Val  Asp  Gly  Pro  Thr  Pro  His  Gln  Thr
785                      790                     795                          800

Val  Arg  Leu  Glu  Asp  Leu  Asp  Glu  Ser  Gly  Ser  Tyr  Trp  Val  Ser  Asp
                    805                     810                          815

Lys  Arg  Leu  Pro  Pro  Cys  Ser  Leu  Ser  Gln  Ala  Leu  Thr  Tyr  Ser  Pro
               820                     825                     830

Asp  Ile  Thr  Thr  Pro  Pro  Thr  Gln  Leu  Leu  Leu  Gln  Lys  Leu  Ala  Gln
          835                     840                     845

Val  Ala  Thr  Glu  Glu  Pro  Glu  Arg  Gln  Arg  Leu  Glu  Ala  Leu  Cys  Gln
     850                     855                     860

Pro  Ser  Glu  Tyr  Ser  Lys  Trp  Lys  Phe  Thr  Asn  Ser  Pro  Thr  Phe  Leu
865                      870                     875                          880

Glu  Val  Leu  Glu  Glu  Phe  Pro  Ser  Leu  Arg  Val  Ser  Ala  Gly  Phe  Leu
                    885                     890                          895

Leu  Ser  Gln  Leu  Pro  Ile  Leu  Lys  Pro  Arg  Phe  Tyr  Ser  Ile  Ser  Ser
               900                     905                     910

Ser  Arg  Asp  His  Thr  Pro  Thr  Glu  Ile  His  Leu  Thr  Val  Ala  Val  Val
          915                     920                     925

Thr  Tyr  His  Thr  Gly  Asp  Gly  Gln  Gly  Pro  Leu  His  His  Gly  Val  Cys
     930                     935                     940

Ser  Thr  Trp  Leu  Asn  Ser  Leu  Lys  Pro  Gln  Asp  Pro  Val  Pro  Cys  Phe
945                      950                     955                          960

Val  Arg  Asn  Ala  Ser  Ala  Phe  His  Leu  Pro  Glu  Asp  Pro  Ser  His  Pro
                    965                     970                          975

Cys  Ile  Leu  Ile  Gly  Pro  Gly  Thr  Gly  Ile  Val  Pro  Phe  Arg  Ser  Phe
               980                     985                     990

Trp  Gln  Gln  Arg  Leu  His  Asp  Ser  Gln  His  Lys  Gly  Val  Arg  Gly  Gly
               995                     1000                    1005

Arg  Met  Thr  Leu  Val  Phe  Gly  Cys  Arg  Arg  Pro  Asp  Glu  Asp  His  Ile
          1010                    1015                    1020
```

```
Tyr Gln Glu Glu Met Leu Glu Met Ala Gln Lys Gly Val Leu His Ala
1025                1030            1035                1040

Val His Thr Ala Tyr Ser Arg Leu Pro Gly Lys Pro Lys Val Tyr Val
            1045                1050                    1055

Gln Asp Ile Leu Arg Gln Gln Leu Ala Ser Glu Val Leu Arg Val Leu
            1060                1065            1070

His Lys Glu Pro Gly His Leu Tyr Val Cys Gly Asp Val Arg Met Ala
            1075            1080                1085

Arg Asp Val Ala His Thr Leu Lys Gln Leu Val Ala Ala Lys Leu Lys
        1090                1095            1100

Leu Asn Glu Glu Gln Val Glu Asp Tyr Phe Phe Gln Leu Lys Ser Gln
1105                1110            1115                1120

Lys Arg Tyr His Glu Asp Ile Phe Gly Ala Val Phe Pro Tyr Glu Ala
                1125            1130            1135

Lys Lys Asp Arg Val Ala Val Gln Pro Ser Ser Leu Glu Met Ser Ala
            1140            1145            1150

Leu
```

ISOLATED HUMAN INDUCIBLE NITRIC OXIDE SYNTHASE

This is a division, of U.S. application Ser. No. 08/314,917, filed on Sep. 28, 1994, now issued as U.S. Pat. No. 5,468,630, which is a continuation of U.S. application Ser. No. 07/981,344, filed Nov. 25, 1992, now abandoned.

BACKGROUND OF THE INVENTION

The invention described herein was made in the course of work supported in part by Public Health Service, Grant Nos. GM44100 and GM37753 from the National Institutes of Health, General Medical Sciences.

The following microorganisms have been deposited by David A. Geller on behalf of the University of Pittsburgh of the Commonwealth System of Higher Education, Pittsburgh, Pa. 15260, USA, on Nov. 18, 1992, with and are available from the permanent collection of the American Type Culture Collection (ATCC), 12301 Parklawn Drive, Rockville, Md. 202852-1776, USA:

ATCC 75358 Human Hepatoacyte Inducible Nitric Oxide Synthase cDNA in pBluescript (pHINOS)

ATCC 69126 Human Hepatocyte Inducible Nitric Oxide Synthase cDNA in pBluescript transformed in *E. coli* SOLR bacteria (plasmid HINOS cDNA)

The American Type Culture Collection has performed viability tests on each of the hereinbefore mentioned deposited microorganisms and has concluded on Nov. 20, 1992, that each of the hereinbefore mentioned deposited microorganisms is viable and capable of reproduction.

These deposits are available to the public upon the grant of a patent to the assignee, the University of Pittsburgh of the Commonwealth System of Higher Education, disclosing them. However, it should be understood that the availability of these deposits does not constitute a license to practice this invention in derogation of patent rights granted by governmental action.

FIELD OF THE INVENTION

This invention relates to a human tissue inducible nitric oxide synthase cDNA clone capable of expressing a human inducible nitric oxide synthase protein, and a process suitable for cloning a cDNA encoding amino acid sequences for the human inducible nitric oxide synthase. More specifically, this invention relates to a human hepatocyte inducible nitric oxide synthase cDNA clone and to a process for cloning and expression of the human hepatocyte inducible nitric oxide synthase cDNA to provide a source of the human hepatocyte inducible nitric oxide synthase enzyme.

This invention provides a process for cloning a cDNA having an amino acid sequence coding for the human hepatocyte inducible nitric oxide synthase. SEQ ID NO: 1 in the SEQUENCE LISTING contains the 4,145 nucleotide bases for the sense strand of cDNA for human hepatocyte inducible nitric oxide synthase and sets forth the base codes as triplets (codon) for the coding parts of the nucleotide sequence. SEQ ID NO: 1 sets forth the amino acid sequence for the cDNA clone for human hepatocyte inducible nitric oxide synthase encoding amino acids 1 through 1153 of the human hepatocyte inducible nitric oxide synthase enzyme.

BACKGROUND OF THE INVENTION

It is known by those skilled in the art that nitric oxide (NO) is a biologic mediator derived from the amino acid L-arginine. One of a family of enzymes, nitric oxide synthase (NOS), acts upon L-arginine to oxidize one of the guanidino nitrogens to NO while citrulline is formed from the remainder of the L-arginine molecule. Nitric oxide is a very short-lived free radical and is rapidly oxidized to nitrite ($NO_2^-$) and nitrate ($NO_3^-$) which is measured as the stable inactive end products of nitric oxide formation.

It is well known by those skilled in the art that multiple isoforms of the nitric oxide synthase enzyme exist and that they are generally classified into two broad categories: 1) constitutive and 2) inducible. These classes of NOS enzymes vary considerably in their size, amino acid sequence, activity and regulation. For example, cells such as neurons and vascular endothelial cells contain constitutive NOS isotypes while macrophages and vascular smooth muscle cells express an inducible NOS.

It is generally well known that small amounts of NO generated by a constitutive NOS appear to act as a messenger molecule by activating soluble guanylate cyclase and, thus, increasing intracellular guanosine, 3', 5'-cyclic monophosphate (cGMP) and the induction of biological responses that are dependent on cGMP as a secondary messenger. For example, through this mechanism, endothelial derived NO induces relaxation of vascular smooth muscle and is identified as endothelium derived relaxing factor (EDRF). *Nature*, Vol. 327, pp. 524–526 (1987) and *Proc Natl Acad Sci USA*, Vol. 84, pp. 9265–9269 (1987). Another example includes, but is not limited by, neuronal nitric oxide which acts as a neuro transmitter by activating guanylate cyclase with important functions in the central nervous system and autonomic nervous systems. *Proc Natl Acad Sci USA*, Vol. 86, pp. 9030–9033 (1989) and *Science*, Vol. 257, p. 401 (1992).

It is generally known by those skilled in the art that the larger quantities of nitric oxide produced by the inducible nitric oxide synthase have antimicrobial and antitumor functions. *J. Clin. Invest.*, Vol. 81, pp. 1129–1136 (1989) and *Science*, Vol. 235, pp. 473–476 (1987), respectively. It is also known by those skilled in the art that when vascular smooth muscle cells are stimulated to express a NOS enzyme by inflammatory cytokines, the excess amounts of nitric oxides that are produced contribute to the vascular collapse seen in sepsis. *FEBS Lett.*, Vol. 265, pp. 133–136, (1990).

Thus, it will be appreciated that nitric oxide has both normal physiologic intracellular and extracellular regulatory functons. However, excessive production of nitric oxide is detrimental. For example, stimulation of inducible nitric oxide synthesis in blood vessels by bacterial endotoxin such as for example bacterial lipopolysaccharide (LPS) and cytokines that are elevated in sepsis results in massive dilation of blood vessels and sustained hypotension commonly encountered in septic shock. *Proc. Natl. Acad. Sci USA*, Vol. 87, pp. 3629–32 (1990). It is known that overproduction of nitric oxide in the lungs stimulated by immune complexes directly damages the lung. *J. Immunol.*, Vol. 148, p. 3086 (1992). Induction of nitric oxide synthase in pancreatic islets impairs insulin secretion and contributes to the onset of juvenile diabetes. *J. Biol. Chem.*, Vol. 266, p. 21351 (1991).

It will be appreciated that there is a great need in the medical community for collective inhibition of the inducible form of NOS but not the constitutive types of NOS in humans because this would allow for a neans of preventing, such as for example, the hypotensive shock seen in sepsis, without preventing the physiologic regulation of vasomotor tone or neuro transmission in the central nervous system.

We recently demonstrated that nitric oxide biosynthesis is induced in isolated human hepatocytes after stimulation with interleukin-1, tumor necrosis factor-alpha, interferon-gamma and bacterial lipopolysacharride (bacterial endotoxin). *FASEB JOURNAL*, Vol. 6, No. 5, page A1834 (April, 1992) and *J. Exp. Med.*, Vol. 176, p. 261 (1992). Heretofore no human cell type was known to show increased production of nitrogen oxides when treated with cytokines. *Res. Immunol.*, Vol. 142, p. 557 (1991). It is generally known by those skilled in the art that all attempts to induce nitric oxide synthase in human macrophages and related cells typical to those found in rodent macrophages have failed. *Res. Immunol.*, Vol. 142, p. 562, 589–90 (1991).

In spite of this background material, there remains a very real and substantial need for a cDNA clone for human tissue inducible nitric oxide synthase and a process for the molecular cloning of the same.

SUMMARY OF THE INVENTION

The present Invention has met the hereinbefore described needs. The present Invention provides a cDNA clone for human tissue inducible nitric oxide synthase and a process for preparing the same.

More specifically, this invention provides a cDNA clone for human hepatocyte inducible nitric oxide synthase and a process for preparing the same. This process includes inducing nitric oxide synthase in human hepatocytes, identifying human hepatocyte nitric oxide synthase messenger RNA, isolating the human hepatocyte nitric oxide synthase messenger RNA, collecting the human hepatocyte nitric oxide synthase messenger RNA, separating human hepatocyte poly A messenger RNA from the human hepatocyte nitric oxide synthase messenger RNA, constructing a cDNA library for human hepatocyte nitric oxide synthase, screening this cDNA library for human hepatocyte inducible nitric oxide synthase cDNA clones, and converting the human hepatocyte inducible nitric oxide synthase cDNA clones to a plasmid vector for obtaining a substantially full length cDNA clone encoding human hepatocyte inducible nitric oxide synthase. This process further includes sequencing this cDNA, expressing the human hepatocyte inducible nitric oxide synthase cDNA protein in an expression system, and purifying the human hepatocyte inducible nitric oxide synthase cDNA protein.

It is an object of the present invention to provide for the molecular cloning and characterization of an inducible nitric oxide synthase in human tissues.

It is an object of the present invention to provide for the molecular cloning and characterization of an inducible nitric oxide synthase in human hepatocytes.

It is an object of the present invention to isolate a cDNA clone for human tissue inducible nitric oxide synthase.

It is an object of the present invention to isolate a cDNA clone for human hepatocyte inducible nitric oxide synthase.

It is an object of the present invention to provide a process for expressing and purifying human tissue inducible nitric oxide synthase enzyme.

It is an object of the present invention to provide a process for expressing and purifying human hepatocyte inducible nitric oxide synthase enzyme.

It is an object of this invention to provide for the regulation of gene expression for the human hepatocyte inducible nitric oxide synthase enzyme.

It is an object of this invention to provide for a protein including a human inducible nitric oxide synthase substantially free of other human proteins.

These and other objects of the invention will be more fully understood from the following description of the invention, the sequence listing and the claims appended hereto.

DETAILED DESCRIPTION OF THE INVENTION

As used herein, the term "patient" includes members of the animal kingdom including but not limited to human beings.

Nitric oxide is a biologic mediator derived from amino acid L-arginine. Nitric oxide synthase (NOS) acts upon L-arginine to oxidize one of the guanidino nitrogens to nitric oxide while citrulline is formed from the remainder of the L-arginine molecule. While it is understood by those skilled in the art that nitric oxide has both normal physiologic intracellular and extracellular regulatory functions, excessive production of nitric oxide is detrimental. It will be appreciated by those skilled in the art that there are no other readily available sources of human tissue inducible nitric oxide synthase. The present invention provides a cDNA clone for human tissue inducible nitric oxide synthase and a process for preparing the same. Therefore, the cloning and expression of a human tissue nitric oxide synthase cDNA of the present invention provides for a source of the enzyme for developing selective inhibitors of nitric oxide synthase.

The cloning and expression of a human tissue nitric oxide synthase cDNA of the present invention provides for a source of the enzyme in a sufficiently high concentration for providing a therapeutic purpose.

In one embodiment of this invention, a process for preparing a cDNA clone coding or a human tissue inducible nitric oxide synthase is provided. This process includes inducing the human tissue nitric oxide synthase in vitro, identifying the human tissue nitric oxide synthase messenger RNA (mRNA) by employing a cDNA probe capable of hybridizing with the human tissue inducible nitric oxide synthase mRNA, isolating the human tissue nitric oxide synthase mRNA, collecting the human tissue nitric oxide synthase mRNA, separating human tissue poly A mRNA from the human tissue nitric oxide synthase mRNA, constructing a human tissue inducible nitric oxide synthase cDNA library from the human tissue poly A mRNA using a reverse transcriptase enzyme and inserting a strand of the cDNA into a phage vector, screening the cDNA library for human tissue inducible nitric oxide synthase clones including incubating the phage vector containing the cDNA with a bacteria for forming at least one positive plaque containing the cDNA clone for human tissue inducible nitric oxide synthase, rescuing the cDNA clone from the phage vector by employing a helper phage, and converting the rescued cDNA clone to a plasmid vector for obtaining a substantially full length cDNA clone encoding human tissue inducible nitric oxide synthase.

In another embodiment of this invention, this process, as hereinbefore described, further includes excising cDNA inserts for human tissue inducible nitric oxide synthase from the plasmid vector. This process also includes confirming the cDNA inserts by employing a dideoxynucleotide DNA sequencing. Further, this process includes confirming the cDNA inserts by employing Southern blot hybridization.

In another embodiment of this invention, the process, as hereinbefore described, includes expressing the human tissue inducible nitric oxide synthase cDNA protein in an expression system, such as for example, a bacterial expression system or a mammalian expression system.

It will be appreciated by those skilled in the art that the cloned human inducible nitric oxide synthase cDNA obtained through the methods described herein may be recombinantly expressed by molecular cloning into an expression vector containing a suitable promoter and other appropriate transcription regulatory elements, and transferred into prokaryotic or eukaryotic host cells to produce recombinant inducible nitric oxide synthase. Techniques for such manipulations are fully described in Maniatis, et al., infra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as for example bacteria, bluegreen algae, plant cells, insect cells and animal cells.

Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis A strong promoter is one which causes mRNAs to be initiated at high frequency. Expression vectors may include, but are not limited to, cloning vectors, modified cloning vectors, specifically designed plasmids or viruses. A variety of mammalian expression vectors may be used to express recombinant inducible nitric oxide synthase in mammalian cells.

Commercially available bacterial expression vectors which may be suitable for recombinant inducible nitric oxide synthase expression, include but are not limited to, pKC30 (ATCC 37286), pPLa2311 (ATCC 31694), pBR322 (ATCC 31344 and 37017), ptac12 (ATCC 37138), lambda gt11 (ATCC 37194), pAS1 (ATCC39262), pLC24, pSB226, SV40 and pKK 223-3.

Commercially available mammalian expression vectors which may be suitable for recombinant inducible nitric oxide synthase expression, include but are not limited to, pBC12B1 (ATCC 67617), pMC1neo (Stratagene), pXTI (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and lambda ZD35 (ATCC 37565).

DNA encoding inducible nitric oxide synthase may also be cloned into an expression vector for expression in a recombinant host cell. Recombinant host cells may be prokaryotic or eukaryotic, including but not limited to bacteria, yeast, mammalian cells including but not limited to cell lines of human, bovine, porcine, monkey and rodent origin, and insect cells including but not limited to drosophila derived cell lines. Cell lines derived from mammalian species which may be suitable and which are commercially available, include but are not limited to, CV-1 (ATCC CCL70), COS-1 (ATCC CRL1650), COS-7 (ATCC CRL1651), CHO-K1 (ATCC CCL61), 3T3 (ATCC CCL92), NIH/3T3 (ATCC CRL 1658), HeLa (ATCC CCL2), C1271 (ATCC CRL1616), BS-C-1 (ATCC CCL26) and MRC-5 (ATCC CCL171). The bacterial cell most used for expression of recombinant protein is *Escherichia coli*. There are various strains of *E. coli* available and are well known in the art.

The expression vector may be introduced into host cells via any one of a number of techniques including but not limited to transformation, transfection, protoplast fusion, and electroporation.

In a preferred embodiment of this invention, the process, as hereinbefore described, includes expressing the human tissue inducible nitric oxide synthase protein in a baculovirus expression system.

Another embodiment of this invention provides for a process, as hereinbefore described, including purifying the human tissue inducible nitric oxide synthase protein.

In a preferred embodiment of this invention, the process, as hereinbefore described, includes employing as the human tissue inducible nitric oxide synthase a human hepatocyte inducible nitric oxide synthase. This process further includes employing as the human tissue inducible nitric oxide synthase protein a human hepatocyte inducible nitric oxide synthase protein.

In another embodiment of this invention, a process is provided, as hereinbefore described, including inducing the human tissue nitric oxide synthase in vitro by stimulating a human tissue in vitro with at least one of the following (1) at least one cytokine, such as for example a cytokine selected from the group consisting of tissue necrosis factor (TNF), interleukin-1 (IL-1), and interferon-gamma (IFN-g), (2) at least one bacterial endotoxin including, such as for example, a bacterial lipopolysaccharide (LPS) and (3) combinations thereof.

A further preferred embodiment of this invention provides a process, as hereinbefore described, that includes constructing a human tissue inducible nitric oxide synthase cDNA library from the human tissue poly A mRNA using a reverse transcriptase enzyme and inserting a cDNA strand having a length of about at least 1,000 base pairs into the phage vector. In yet another preferred embodiment, a process is provided, as hereinbefore described, that includes employing lambda Zap II as the phage vector.

In another embodiment of this invention, a process is provided, as hereinbefore described, including screening the cDNA library including incubating the phage vector for about 6 to 24 hours with a bacteria at a temperature from about 34 to 40 degrees centigrade for effectuating phage lysis of the bacteria. This process further includes rescuing the cDNA clone from the phage vector by employing a helper phage such as for example ExAssist helper phage (Stratagene, La Jolla, Calif.).

In a preferred embodiment of this invention, a process, as hereinbefore described, is provided including converting the rescued cDNA clone to the plasmid vector for obtaining a substantially full length cDNA clone encoding the human tissue inducible nitric oxide synthase wherein the plasmid vector includes pBluescript (Stratagene, La Jolla, Calif.).

In another preferred embodiment of this invention, a process as hereinbefore described is provided including employing as the human tissue inducible nitric oxide synthase a human hepatocyte inducible nitric oxide synthase.

Another embodiment of this invention provides for a process for producing human hepatocyte inducible nitric oxide synthase protein comprising providing a replicatable DNA expression vector capable of expressing a DNA sequence encoding human hepatocyte inducible nitric oxide synthase in a suitable host, transforming the host for obtaining a recombinant host, and maintaining the recombinant host under conditions permitting expression of the DNA sequence to provide human hepatocyte inducible nitric oxide synthase.

Another embodiment of this invention provides a human tissue inducible nitric oxide synthase cDNA clone. A preferred embodiment of this invention provides a human hepatocyte inducible nitric oxide synthase cDNA clone. The human hepatocyte inducible nitric oxide synthase cDNA clone of this invention has a cDNA coding for the amino acid sequence, SEQ ID NO: 1.

The cDNA double strand sequence was determined using the Sanger dideoxynucleotide sequence technique well known by those skilled in the art on a Genesis 2000 sequencing system (USB, Cleveland, Ohio). *Proc. Natl. Acad. Sci. USA*, Vol 74, p. 5463 (1977).

Another embodiment of this invention provides a human tissue inducible nitric oxide synthase recombinant protein expressed from a human tissue inducible nitric oxide synthase cDNA clone. In a preferred embodiment, a human hepatocyte inducible nitric oxide synthase recombinant protein expressed from a human hepatocyte inducible nitric oxide synthase cDNA clone is provided.

Another embodiment of this invention provides for a protein comprising a human inducible nitric oxide synthase substantially free of other human proteins.

Another embodiment of this invention provides for an isolated DNA sequence encoding human inducible nitric oxide synthase consisting essentially of an initiation codon positioned upstream and adjacent to an open reading frame consisting essentially of a DNA sequence encoding human inducible nitric oxide synthase.

A further embodiment of this invention provides for an isolated DNA sequence encoding human inducible nitric oxide synthase consisting essentially of an initiation codon positioned upstream and adjacent to an open reading frame consisting essentially of a DNA sequence encoding human inducible nitric oxide synthase protein. The human inducible nitric oxide synthase protein begins at the initiation codon and terminates at a stop codon.

In yet another embodiment of this invention a recombinant plasmid is provided containing a recombinant plasmid pHINOS having a deposit accession number ATCC 75358 deposited with the American Type Culture Collection. A further embodiment of this invention provides for bacteria transformed by the recombinant plasmid pHINOS.

In another embodiment of this invention a microorganism is provided containing a HINOS cDNA plasmid transformed in *E. coli* SOLR bacteria having a deposit accession number ATCC 69126 deposited with the American Type Culture Collection.

EXAMPLE 1

Inducing Human Hepatocyte Inducible Nitric Oxide Synthase mRNA is weakly induced following stimulation with cytokine signals such as for example tumor necrosis factor (TNF), interleukin-1 (IL-1) or interleukin-gamma (IFN-g). Cytokine signals synergize to further up-regulate mRNA levels and nitric oxide synthase activity. Maximum induction was achieved with a combination of TNF, IL-1, IFN-g and bacterial lipopolysaccharide (LPS). *FASEB, Journal*, Vol. 6, supra, and *J. Exp. Med.*, Vol. 176, supra.

EXAMPLE 2

Identifying and Isolating Human Hepatocyte Nitric Oxide Synthase mRNA

A cDNA probe capable of hybridizing with human hepatocyte inducible nitric oxide synthase mRNA was used for identifying and isolating the mRNA for human hepatocyte inducible nitric oxide synthase. The time-point of peak mRNA levels following cytokine and LPS [hereinafter cytokine mixture (CM)] stimulation was then determined.

Total RNA was extracted about 2–48 hours following CM-stimulation of cultured human hepatocytes using the RNAzol B modified method of Chomczynski and Sacchi. *Anal Biochem.*, Vol 162; pp. 156–159 (1987). Northern blot analysis was performed on 20 microgram (ug) aliquots of total RNA using a murine macrophage cDNA probe, representing an excision fragment produced by Not I restriction enzyme [*Proc. Natl. Acad. Sci. USA.*, Vol 89, pp. 6711–6715 (1992) GenBank Accession No. M926491] and cross-species hybridization. The human hepatocyte nitric oxide synthase mRNA was identified as a single band at about 4.5 kb (kilobase) with maximal mRNA levels seen about 8 hours after stimulation.

Human hepatocytes (HC) that were freshly isolated were placed in cell culture and exposed to a combination of human recombinant tumor necrosis factor (500 units/milliliter), human recombinant interleukin-1 (5 units/milliliter), human recombinant interferon-gamma (100 units/milliliter), and lipopolysaccharide (10 micrograms/milliliter). At (2 hours, 4 hours, 6 hours and 8 hours, total RNA was isolated and 20 micrograms per sample was subjected to Northern Blot analysis. A 2.7 Kb fragment of cDNA to murine macrophage inducible nitric oxide synthase was used to hybridize with the mRNA for human hepatocyte inducible nitric oxide synthase. The data indicate that the 4.5 Kb message peaked at about 8 hours following stimulation. Furthermore no mRNA signal was detected in control (unstimulated) hepatocytes. The expression of the 4.5 Kb mRNA for human hepacocyte inducible nitric oxide synthase at about 8 hours after exposure to the above mentioned signals for hepatocytes isolated from three separate individuals was monitored signal was detected in control (unstimulated) hepatocytes.

Because the 8 hour time point yielded maximal mRNA levels, samples of RNA were isolated from two human livers about 8 hours following CM-stimulation in vitro and were pooled to obtain sufficient quantity for the cDNA library construction. The cDNA synthesis requires about from 10 to 20 micrograms of poly A mRNA rather than total RNA. To obtain purified poly A mRNA, poly A mRNA was separated from total RNA by elution through an oligo-dT cellulose column. The purity of the mRNA was assessed by repeat Northern blot analysis which included subjecting 0.5 micrograms of poly A RNA from each of the two human livers to Northern Blot analysis using the 2.7 Kb cDNA from murine macrophage inducible nitric oxide synthase. The data also demonstrate strong nitric oxide synthase mRNA expression from 2 different patients without evidence of degraded poly A RNA.

The data demonstrate that the murine macrophage inducible nitric oxide synthase cross hybridizes with the human hepatocyte inducible nitric oxide synthase poly A RNA and effectively identifies the mRNA for human hepatocyte inducible nitric oxide synthase. These samples of poly A RNA were used to construct the cDNA library for isolation of the cDNA clone for the human hepatocyte inducible nitric oxide synthase.

EXAMPLE 3

Constructing a Human Hepatocyte Inducible Nitric Oxide Synthase cDNA Library

Using about 20 micrograms of poly A RNA enriched for hepatocyte nitric oxide synthase mRNA by CM-stimulation, a cDNA library was constructed by Stratagene, La Jolla, Calif. The first strand cDNA was synthesized from the human hepatocyte poly A RNA using reverse transcriptase enzyme with random and oligo-dT primers. After size exclusion for a minimum of about 1000 nucleotide base pair length, the cDNA's were inserted into a lambda Zap II phage vector (Stratagene, La Jolla, Calif.) and was titered.

EXAMPLE 4

Screening the cDNA Library for Human Hepatocyte Inducible Nitric Oxide Synthase cDNA Clones To screen the cDNA library, $1 \times 10^6$ phage were incubated with bacteria (*E. coli* Sure strain) at about 34 to 40 degrees centigrade for about 15 to 30 minutes. This mixture was added to molten agarose and poured onto 20×20 centimeter agar plates at a density of about $2 \times 10^5$ plaques/plate (Maniatis et al., *Molecular Cloning: A Laboratory Manual*, Cold Spring Harbor Laboratory, Cold Spring Harbor, N.Y., 1982). The plates were incubated from about 34 to 40 degrees centigrade overnight from about 6 to 24 hours to allow for phage lysis of bacteria. The plaques were then transferred to nylon filters and positive clones were identified by filter hybridization with $^{32}$P-labeled murine macrophage nitric oxide synthase cDNA probe. Positive clones were cored from the agar plates after localization by autoradiograph alignment. This procedure was repeated about 3 times until individual clones were isolated. The positive clones were rescued from the lambda Zap II phage vector using a helper phage ExAssist (Stratagene, La Jolla, Calif.), and then converted to the plasmid vector, pBluescript (Stratagene, La Jolla, Calif.). The cDNA inserts for human hepatocyte inducible nitric oxide synthase were excised from the Bluescript plasmid cloning sites by restriction analysis with EcoRI enzyme and then sized by gel electrophoresis. The cDNA insert identities were confirmed by DNA sequencing and by Southern blot hybridization with the murine macrophage cDNA clone. In addition, repeat Northern blot analysis was performed on cytokine-stimulated human hepatocytes in culture using the human nitric oxide synthase cDNA clone of this invention as probe. The time course for mRNA expression for human hepatocyte inducible nitric oxide synthase. From an individual patient different from the patients listed above was measured, and the cells were exposed to the same agents as described in Example 2. The results of these experiments demonstrate the human nitric oxide synthase cDNA identifying the same mRNA signal as the macrophage probe, thus, further confirming its identify. Furthermore, the results demonstrate that the inOs message peaked at about 8 hours after exposure to the inducing factors and was detectable up to 48 hours post inducement. No iNOS mRNA was detected from control (unstimulated) cells. It is important to note that the isolated cDNA clone coding for human inducible nitric oxide synthase of this invention was used to hybridize with the mRNA, thus, confirming the capacity of the cDNA clone of this invention to identify the human hepatocyte inducible nitric oxide synthase mRNA.

EXAMPLE 5 cDNA Sequencing

The plasmid vector pbluescript contains universal primer regions which were used to facilitate double-stranded DNA sequencing. Positive clones were sequenced by using the dideoxynucleotide technique of Sanger, supra, with the Genesis 2000 sequencing system (USB, Cleveland, Ohio). Sequence analysis was done using Genbank DNA sequencing software programs available through the Pittsburgh Supercomputing Center (Billiar TR., Pittsburgh Supercomputing Center, Pittsburgh, Pa.).

EXAMPLE 6

Expressing Human Hepatocyte Inducible Nitric Oxide Synthase

Verification of the full length cDNA identify was accomplished by expressing the recombinant human hepatocyte inducible nitric oxide synthase protein. The human hepatocyte inducible nitric oxide synthase clone was ligated into the pCIS expression vector (Genentech, Calif.) which utilizes a CMV promoter. Next the expression vector was transfected into human embryonic kidney 293 cells (ATCC, Maryland). Nitric oxide synthase activity was assessed by measuring the conversion of [$^3$H] arginine to [$^3$H] citrulline. It will be appreciated by those skilled in the art that this expression system was successfully used for expression of the cloned rat brain constitutive nitric oxide synthase, and there was negligible nitric oxide synthase activity in the unstimulated 293 kidney cells [Bredt et al., *Nature*, Vol 351, p. 714 (1991)]. After the identity of the human hepatocyte inducible nitric oxide synthase clone of this invention was verified as hereinbefore described, the cDNA was expressed in a baculovirus expression system (Invitrogen, San Diego, Calif.) which allowed for large scale enzyme production. *Texas Agriculture Experiment Station Bulletin*, No. 1555 (1988). More specifically, the human hepatocyte nitric oxide synthase cDNA was inserted into the baculovirus transfer vector and then co-transfected with wild type viral DNA into Sf9 insect cells (ATCC, Maryland). Recombinant viral plaques were isolated to allow for protein over-expression.

EXAMPLE 7

Purifying the Human Hepatocyte Inducible Nitric Oxide Synthase Protein

The resultant human hepatocyte inducible nitric synthase protein was purified using a two step procedure. First, the protein was passed through an anion-exchange column of DEAE cellulose. This was followed by affinity chromatography with 2', 5'-ADP Sepharose. [Evans et al., *Proc. Natl. Acad. Sci. USA*, Vol. 39, pp. 5361–5365 (1992)] Purity was assessed by SDS-polyacrylamide gel electrophoresis. Activity was quantitated after each step by measuring the ability of the enzyme to generate $NO_2^-$ and $NO_3^-$ from L-arginine. $NO_2^-$ and $NO_3^-$ was measured using an automated calorimetric reaction based on the Greiss reaction [Green et al., *Anal. Biochem.*, Vol. 126, p. 131 (1982)].

Whereas, particular embodiments of this invention have been described above for purposes of illustration, it will be evident to those persons skilled in the art that numerous variations of the details of the present invention may be made without departing from the invention as defined in the appended claims that follow the SEQUENCE LISTING.

What is claimed:

1. An isolated recombinant human inducible nitric oxide synthase.

2. The isolated recombinant human inducible nitric oxide synthase of claim 1 which is expressed from a cDNA clone.

3. The isolated recombinant human inducible nitric oxide synthase of claim 1 having the amino acid sequence as set forth in SEQ ID NO:2.

4. An isolated recombinant human hepatocyte inducible nitric oxide synthase.

5. The isolated recombinant human hepatocyte inducible nitric oxide synthase of claim 4 which is expressed from a cDNA clone.

6. A substantially purified, or isolated, naturally-occurring human inducible nitric oxide synthase.

7. The substantially purified, or isolated, naturally-occurring human inducible nitric oxide synthase of claim 6 which is a human hepatocyte inducible nitric oxide synthase.

8. The substantially purified, or isolated, naturally-occurring human inducible nitric oxide synthase of claim 6 having the amino acid sequence as set forth in SEQ ID NO:2.

9. A substantially purified protein comprising an amino acid sequence for human inducible nitric oxide synthase.

10. The protein of claim 9 wherein said human inducible nitric oxide synthase is a human hepatocyte inducible nitric oxide synthase.

11. The protein of claim 9 wherein said human inducible nitric oxide synthase has the amino acid sequence as set forth in SEQ ID NO:2.

* * * * *

UNITED STATES PATENT AND TRADEMARK OFFICE
CERTIFICATE OF CORRECTION

PATENT NO. : 5,882,908
DATED : March 16, 1999
INVENTOR(S) : Timothy R. Billiar; Andreas K. Nussler; David A. Geller; Richard L. Simmons It is certified that errors appear in the above-identified patent and that said Letters Patent is hereby corrected as shown below:

ON THE TITLE PAGE:

In References Cited, line 4: "Billiur" should read --Billiar--

In Other Publications, line 16: "Kie" should read --Xie--

In Other Publications, Column 2, line 6: "1987" should read --1988--

In Other Publications, Page 2, Column 1, line 47: "Dusease" should read -- Disease--

IN THE SPECIFICATION:

In Column 1, line 22: "Hepatoacyte" should read --Hepatocyte--

In Column 1, line 59: "SEQ ID NO:1" should read --SEQ ID NOS: 1 and 2--

In Column 2, line 47: "functons" should read --functions--

In Column 2, line 64: "neans" should read --means--

In Column 3, line 20: "Invention" should read --invention--

In Column 3, line 21: "Invention" should read --invention--

In Column 4, line 15: "physologic" should read --physiologic--

In Column 4, line 31: "or" should read -- for--

UNITED STATES PATENT AND TRADEMARK OFFICE
CERTIFICATE OF CORRECTION

PATENT NO.   : 5,882,908
DATED        : March 16, 1999
INVENTOR(S)  : Timothy R. Billiar; Andreas K. Nussler; David A. Geller; Richard L. Simmons It is certified that errors appear in the above-identified patent and that said Letters Patent is hereby corrected as shown below:

IN THE SPECIFICATION:

In Column 5, line 23: "synthesis A" should read --synthesis. A--

In Column 7, line 3: "SEQ ID NO:1" should read --SEQ ID NOS: 1 and 2--

In Column 8, line 22: "At (2 hours" should read --At 2 hours--

In Column 8, line 31: "hepacocyte" should read --hepatocyte--

In Column 8, line 34: "monitored signal" should read --monitored. No signal--

In Column 9, line 43: "synthase. From" should read --synthase is from --

In Column 9, line 50: "inOs" should read --iNOS--

In Column 9, line 63: "pbluescript" should read --pBluescript--

In Column 10, line 52: "39" should read --89--

Signed and Sealed this

Thirtieth Day of November, 1999

Q. TODD DICKINSON

Attest:

Attesting Officer

Acting Commissioner of Patents and Trademarks